US008202515B2

(12) United States Patent
Takano et al.

(10) Patent No.: US 8,202,515 B2
(45) Date of Patent: Jun. 19, 2012

(54) METHOD OF PRODUCING DRY YEAST CONTAINING S-ADENOSYL-L-METHIONINE AND COMPOSITION FOR ORAL INTAKE

(75) Inventors: Kentarou Takano, Niigata (JP); Shinyo Gayama, Niigata (JP); Toshito Tsuchida, Kanagawa (JP)

(73) Assignees: Mitsubishi Gas Chemical Company, Inc., Tokyo (JP); Mitsubishi Tanabe Pharma Corporation, Osaka (JP)

( * ) Notice: Subject to any disclaimer, the term of this patent is extended or adjusted under 35 U.S.C. 154(b) by 778 days.

(21) Appl. No.: 12/299,942

(22) PCT Filed: May 8, 2007

(86) PCT No.: PCT/JP2007/059498

§ 371 (c)(1), (2), (4) Date: Nov. 7, 2008

(87) PCT Pub. No.: WO2007/129701

PCT Pub. Date: Nov. 15, 2007

(65) Prior Publication Data

US 2009/0181001 A1 Jul. 16, 2009

(30) Foreign Application Priority Data

May 10, 2006 (JP) ................................ 2006-131764

(51) Int. Cl.
*A01N 63/00* (2006.01)

(52) U.S. Cl. .................................................... 424/93.51

(58) Field of Classification Search ................ 424/93.51
See application file for complete search history.

(56) References Cited

U.S. PATENT DOCUMENTS 4,057,686 A 11/1977 Fiecchi

FOREIGN PATENT DOCUMENTS

| | | |
|---|---|---|
| GB | 1436509 | 5/1976 |
| JP | 51-125717 | 11/1976 |
| JP | 05-328988 | 12/1993 |
| JP | 2005-229812 | 9/2005 |
| UK | 2116172 | 9/1983 |
| WO | WO 01/90130 | 11/2001 |
| WO | WO 2004/067758 | 8/2004 |

OTHER PUBLICATIONS

Zhou et al., "Liquid Chromatographic Determination of S-Adenosyl-L-Methione in Dietary Supplement Tablets", J AOC Int, 2002, vol. 85, No. 4, pp. 901-905.

Extended European Search Report, including Supplementary European Search and European Search Opinion, dated Oct. 2, 2009, for Application No. EP 07 74 2933.

A. Morana, et al., "Stabilization of S-adenosyl-L-methionine promoted by trehalose" *Biochimica et Biophysica Acta*, 1573 (2002), pp. 105-108.

S. Shiozaki, et al., "Unusual Intracelluar Accumulation of S-Adenosyl-L-methionine by Microorganisms" *Agric. Biol. Chem.*, vol. 48, No. 9, 1984, pp. 2293-2300.

*Primary Examiner* — Tekchand Saidha

(74) *Attorney, Agent, or Firm* — Antonelli, Terry, Stout & Kraus, LLP.

(57) ABSTRACT

A method for producing a dry yeast containing S-adenosyl-L-methionine using a yeast having production capability of S-adenosyl-L-methionine, in which a yeast cell concentrate separated from a cell culture liquid of the yeast is subjected to at least one treatment of (1) a treatment of adding a mineral acid to adjust the pH of the concentrate to 1 to 5, and (2) a treatment of heating the concentrate to 40 to 85° C., and then dried, and a composition for oral ingestion containing a dry yeast produced by the production method, having been molded. A method for producing dry yeast cells containing S-adenosyl-L-methionine, which is useful as a water soluble physiologically active substance, in a high concentration with a good yield at low cost, and a composition for oral ingestion formed by molding a dry yeast produced by the production method can be provided.

9 Claims, No Drawings

METHOD OF PRODUCING DRY YEAST CONTAINING S-ADENOSYL-L-METHIONINE AND COMPOSITION FOR ORAL INTAKE

TECHNICAL FIELD

The present invention relates to a method for producing a dry yeast containing S-adenosyl-L-methionine using a yeast having production capability of S-adenosyl-L-methionine (which is hereinafter described as SAMe), and a composition for oral ingestion. More specifically, it relates to a method for producing a dry yeast containing SAMe in a high concentration conveniently with a good yield, and a composition for oral ingestion formed by molding a dry yeast containing SAMe obtained by the method.

BACKGROUND ART

SAMe is a water soluble physiologically active substance that plays an important role as a methyl group donor in methylation reaction with various transmethylases within the living body, and is used widely as a therapeutic medication for depression, liver disorder, arthritis and the like, or health foods. The yeast cell contains useful components including 5'-nucleotide, a free amino acid, glutathione, which has antioxidant action and is utilized as a therapeutic medication for liver disorder, β-glucan, which has immune strength enhancement function and intestinal condition improvement function, dietary fibers and the like, and is utilized widely as health foods.

As the conventional production method of SAMe, such a method has been ordinarily used that SAMe is accumulated in cells by fermentative production using a culture medium containing L-methionine as a precursor (see, for example, Non-patent Documents 1 and 2), is extracted and purified by chromatography, and is formed into a stable SAMe salt, such as a salt with sulfuric acid or p-toluenesulfonic acid or a salt with butanedisulfonic acid (see, for example, Non-patent Documents 3 and 4). In the conventional production method, however, large amounts of labor and cost are required for extraction and purification of SAMe accumulated in cells, and it is difficult to produce SAMe, which is important as a therapeutic medication and health foods, at low cost.

An enzymatic synthesis method, which does not require extraction and purification from cells, is known as a substitute method of the fermentative method. Accordingly, SAMe is enzymatically synthesized with adenosine 5'-triphosphate (ATP) and L-methionine as substrates using a SAMe synthesizing enzyme (methionine adenosyltransferase), which is isolated and purified from microorganisms, such as a yeast (see, for example, Patent Document 1 and Non-patent Documents 5 and 10). As compared to the fermentative method, this method has such advantages that SAMe is accumulated in a large amount, and it is not necessary to extract SAMe from the cells, but has various problems, in which preparation of the enzyme is complicated, the resulting enzyme has weak activity, inhibition enzyme activity, such as ATP degradation activity, is necessarily removed, and ATP as the substrate is considerably expensive, and therefore, the method has not been subjected to practical use. According to development of gene engineering in recent years, the enzyme can be conveniently prepared by using cloned SAMe synthesizing enzyme gene (see, for example, Non-patent Documents 6 to 9) to solve the problem in preparation of the enzyme, but other practical problems, such as the use of expensive ATP as the substrate, have not yet been resolved.

[Patent Document 1] JP-A-51-125717

[Non-patent Document 1] Schlenk F., DePalma R. E., J. Biol. Chem., 229, 1037-1050 (1957)

[Non-patent Document 2] Shiozaki S., et al, Agric. Biol. Chem., 53, 3269-3274 (1989)

[Non-patent Document 3] Schlenk F., DePalma R. E., J. Biol. Chem., 229, 1051-1057 (1957)

[Non-patent Document 4] Kusakabe, H., Kuninaka, A., Yoshino, H., Agric. Biol. Chem., 38, 1669-1672 (1974)

[Non-patent Document 5] Mudd S H., Cantoni G L., etal, J. Biol. Chem., 231, 481-492 (1958)

[Non-patent Document 6] Markham G. D., et al, J. Biol. Chem., 255, 9082-9092 (1980)

[Non-patent Document 7] Markham D J., DeParisis J., J. Biol. Chem., 259, 14505-14507 (1984)

[Non-patent Document 8] Shiozaki S., et al, J. Biotechnology., 4, 345-354 (1986)

[Non-patent Document 9] Thomas D., Surdin-Kerjan Y., J. Biol. Chem., 262, 16704-16709 (1987)

[Non-patent Document 10] Thomas D., Cherest H., et al, Mol. Cell. Biol., 8, 5132-5139 (1988)

DISCLOSURE OF THE INVENTION

As having been described above, the conventional fermentative method using microorganisms requires large amounts of labor and cost for extraction and purification, and the conventional enzymatic method requires large amounts of labor and cost for synthesis. Accordingly, it is considerably difficult to produce a SAMe-containing product capable of being orally ingested at low cost. Therefore, an object of the present invention is to establish a method capable of producing a dry yeast containing SAMe in a high concentration conveniently with a good yield as a method for producing the SAMe-containing product at low cost, and to provide a composition for oral ingestion formed by molding a dry yeast obtained by the production method.

As a result of earnest investigation made by the inventors for attaining the objects, it has been found that the target dry yeast containing SAMe in a high concentration can be produced conveniently at low cost with a high yield in the following manner. A yeast having SAMe production capability capable of being orally ingested is used, and SAMe is synthesized and accumulated in a high concentration in the cells. The yeast cells are then separated from the culture liquid with a separation measure, such as centrifugation, and the liquid is subjected to at least one treatment of a treatment of adding a mineral acid to adjust the pH to a specific value, and a treatment of heating the liquid to a specific temperature. The liquid is then dried. Consequently, the present invention has been completed.

Accordingly, the present invention provides a method for producing a dry yeast containing SAMe in a high concentration, and a composition for oral ingestion formed by molding the dry yeast, shown in the items 1 to 9 below.

1. A method for producing a dry yeast containing S-adenosyl-L-methionine using a yeast having production capability of S-adenosyl-L-methionine, in which a yeast cell concentrate separated from a cell culture liquid of the yeast is subjected to at least one treatment of (1) a treatment of adding a mineral acid to adjust the pH of the concentrate to 1 to 5, and (2) a treatment of heating the concentrate to 40 to 85° C., and then dried.

2. The method for producing a dry yeast containing S-adenosyl-L-methionine according to the item 1, wherein a yeast belonging to *Saccharomyces* is used as the yeast having production capability of S-adenosyl-L-methionine.

3. The method for producing a dry yeast containing S-adenosyl-L-methionine according to the item 2, wherein the yeast belonging to *Saccharomyces* is *Saccharomyces cerevisiae*.

4. The method for producing a dry yeast containing S-adenosyl-L-methionine according to the item 1, wherein the mineral acid used in the treatment of adding a mineral acid (1) is sulfuric acid.

5. The method for producing a dry yeast containing S-adenosyl-L-methionine according to the item 1, wherein in the treatment of adding a mineral acid (1), the pH is adjusted to 1 to 4.

6. The method for producing a dry yeast containing S-adenosyl-L-methionine according to the item 1, wherein in the treatment of heating (2), the concentrate is heated to 40 to 80° C.

7. The method for producing a dry yeast containing S-adenosyl-L-methionine according to the item 1, wherein both the treatment of adding a mineral acid (1) and the treatment of heating (2) are performed.

8. The method for producing a dry yeast containing S-adenosyl-L-methionine according to the item 1, wherein the concentrate is dried by a freeze drying method or a spray drying method.

9. A composition for oral ingestion containing a dry yeast containing S-adenosyl-L-methionine produced by the method according to one of the items 1 to 8, having been molded.

BEST MODE FOR CARRYING OUT THE INVENTION

The kind of the yeast used in the present invention may be one having production capability of SAMe and capable of being orally ingested, and preferred examples thereof include yeasts belonging to *Saccharomyces*. Among these, *Saccharomyces cerevisiae* is more preferred.

Upon culturing the yeast, a carbon source, a nitrogen source, various kinds of inorganic salt, various kinds of additives and the like are used. The carbon source used is not particularly limited as far as it is capable of being utilized by the yeast, and examples thereof include a hydrocarbon, such as glucose, sucrose, starch and blackstrap, and an alcohol and an organic acid, such as ethanol and acetic acid. The nitrogen source is also not particularly limited as far as it is capable of being utilized by the yeast, and examples thereof include an inorganic nitrogen compound, such as ammonia, nitric acid and urea, and those containing an organic nitrogen compound, such as yeast extract and malt extract. Examples of the inorganic salt used include a phosphate salt, a potassium salt, a sodium salt, and a metallic salt, such as magnesium, iron, calcium, zinc, manganese, cobalt, copper and molybdenum. Furthermore, the culture may be performed by adding methionine, adenine and adenosyl ribonucleoside constituting the skeleton of SAMe.

While the culture temperature and the pH of the culture liquid vary depending on the kind of the yeast to be used, the culture temperature may be in a range of from 20 to 35° C., and the pH of the culture liquid may be in a range of from 4 to 7.

Aerobic culture is preferred for increasing the SAMe content in the cells. Accordingly, the culture vessel is preferably aerated and can be stirred depending on necessity, and for example, a mechanically stirred culture vessel, an air-lift type culture vessel, a bubble tower type culture vessel and the like may be used.

Culture components such as the carbon source, the nitrogen source, the various inorganic salts, and the various additives may be added to the culture vessel at one time or individually and continuously or intermittently. For example, the substrate, such as sucrose and ethanol, may be fed to the culture vessel in the form of a mixture with other components of the culture medium, or may be independently added to the culture vessel separately from the other components of the culture medium. The pH of the culture liquid can be controlled with an acid or alkali solution. The alkali for controlling the pH is preferably ammonia and urea, which are used as the nitrogen source, or a non-nitrogen base, such as sodium hydroxide and potassium hydroxide. Examples of the acid used include an inorganic acid, such as phosphoric acid, sulfuric acid and nitric acid, and an organic acid. A phosphate salt, a potassium salt, a sodium salt, a nitrate salt and the like, which are inorganic base, may be used for controlling the pH.

The yeast is cultured under the conditions, and in the stage where the target amount of SAMe is accumulated in the yeast cells, the culture liquid is taken out from the culture vessel and then separated to provide a yeast cell concentrate. The separating method is not particularly limited as far as the cells can be separated and rinsed efficiently, and preferred examples thereof include a counter current yeast separator and an ultrafiltration apparatus using a separation membrane.

The separated yeast cell concentrate is then subjected to at least one of the treatment of adding a mineral acid, such as sulfuric acid, and a treatment of heating. By performing the treatment of adding a mineral acid, the stability of SAMe is improved to enhance the yield. The mineral acid added is not particularly limited as far as it is orally ingested, and examples thereof include hydrochloric acid, sulfuric acid and phosphoric acid, with sulfuric acid being more preferred. The addition amount of the mineral acid is such an amount that provides pH 1 to 5, and preferably such an amount that provides pH 1 to 4.

By performing the treatment of heating, deactivation of SAMe degradation enzyme and sterilization can be attained. The treatment of heating may be performed under such a condition that the SAMe content obtained is increased as much as possible, and the condition for the treatment of heating is, while depending on the heating time, necessarily from 40 to 85° C., preferably from 40 to 80° C., more preferably from 40 to 70° C., and further preferably from 50 to 70° C.

The heating time cannot be determined unconditionally since it varies depending on the heating temperature, and it is preferably from 30 to 600 seconds, and more preferably from 30 to 60 seconds. By performing the treatment of heating for 30 seconds or more, deactivation of SAMe degradation enzyme and sterilization can be attained. Furthermore, permeation of the mineral acid ion is accelerated, whereby the amount of the mineral acid added can be decreased. By performing the treatment of heating for 600 seconds or less, decrease in content of SAMe due to degradation thereof can be prevented from occurring.

The treatment of heating can be performed under either normal pressure or increased pressure. By performing the treatment of heating, or by performing the treatment of adding a mineral acid, such dry yeast cells can be obtained that have a relatively high SAMe content.

It is preferred to perform both the treatment of adding a mineral acid and the treatment of heating since the amount of the mineral acid added can be decreased as compared to the case where only the treatment of adding a mineral acid is performed, and dry cells having a higher SAMe content can be obtained as compared to the case where only the treatment of heating is performed. Specifically, the combination of the addition amount of the mineral acid and the heating temperature is, while depending on the heating time, preferably a combination of an addition amount of the mineral acid providing pH 1 to 5 and a temperature condition of from 40 to 85° C., more preferably a combination of an addition amount of the mineral acid providing pH 1 to 4 and a temperature condition of from 40 to 80° C., further preferably a combination of an addition amount of the mineral acid providing pH 1 to 4 and a temperature condition of from 40 to 70° C., and still further preferably a combination of an addition amount of the mineral acid providing pH 1 to 4 and a temperature condition of from 50 to 70° C.

After performing at least one of the treatment of adding a mineral acid and the treatment of heating, the water content of the resulting yeast cell concentrate is evaporated, for example, by such a drying method as a spray drying method with a spray dryer and a freeze drying method with the final stage temperature of 25° C., thereby providing a dry yeast.

Subsequently, the dry yeast may be pulverized to powder, and another bioactive component and an additive, such as a vehicle, may be added to the dry yeast in the form of powder if needed, which may be then tabletted by compression to provide a composition for oral ingestion in the form of tablet. The surface of the tablet may be coated. The powder may be granulated into a granular form, and the granules thus granulated may be capsulated.

EXAMPLE

The present invention will be described in more detail with reference to examples and comparative examples, but the present invention is not limited to the examples.

Example 1

(a) Culture of Yeast Cells

According to the known culture method (Shiozaki S., et al, J. Biotechnology, 4, 345-354 (1986) (Non-patent Document 8)) described above, yeast cells were cultured by using a 30 L jar culture vessel, produced by Marubishi Bioengineering Co., Ltd. In a culture medium containing components including 10% by mass of sucrose and 1% by mass of yeast extract as a carbon source, 1.8% by mass of urea as a nitrogen source, 1% by mass of L-methionine, 0.2% by mass of L-glycylglycine, 0.4% by mass of $KH_2OP_4$, 0.01% by mass of $MgSO_4.7H_2O$, 2 μg/mL of biotin and 0.2% by mass of mixed minerals (the formulation of the mixed mineral included 2.0% by mass of $CaCl_2.2H_2O$, 0.05% by mass of $MnSO_4.5H_2O$, 0.05% by mass of $FeSO_4.7H_2O$, 0.1% by mass of $ZnSO_4.7H_2O$, 0.001% by mass of $CuSO_4.5H_2O$, 0.001% by mass of $CoCl_2.6H_2O$, 0.001% by mass of $H_3BO_3$, 0.001% by mass of $Na_2MoO_4$ and 0.001% by mass of KI), *Saccharomyces cerevisiae* IFO 2346 belonging to *Saccharomyces* was inoculated and cultured at a culture temperature of from 27 to 29° C. and a stirring rate of 150 rpm under aerophilic aeration for 6 days. Ethanol and $MgSO_4.7H_2O$ that run short during culture were successively added to increase the content of SAMe. Consequently, 18 L of a yeast cell culture liquid having a cell content of 3.5% by mass and a SAMe content of 205 mg per gram of dry yeast was obtained.

(b) Collection of Yeast Cells

18 L of the yeast cell culture liquid was treated with a continuous rotary type centrifugal separator (Hitachi Himac Centrifuge CR1OB2) to provide 3.49 kg of a yeast cell concentrate in the form of liquid having a cell concentration corresponding to 18% by mass in terms of dry yeast.

(c) Addition of Mineral Acid to Yeast Cell Concentrate 224 g of 95% by mass sulfuric acid was added to 3.49 kg of the yeast cell concentrate to provide 3.71 kg of a yeast cell concentrate having pH 1.

(d) Production of Dry Yeast 3.71 kg of the yeast cell concentrate having pH 1 was spray-dried with a spray dryer (produced by Nipro Corporation) having a rotary atomizer (rotary disk) as an atomizer under conditions of an inlet temperature of the drying chamber of from 195 to 205° C., an outlet temperature thereof of from 80 to 90° C. and a liquid feeding rate of 38 g/min to provide 570 g of a powder dry yeast. The resulting powder dry yeast had a SAMe content of 174 mg per gram of dry yeast.

The SAMe content in the powder dry yeast was measured in such a manner that SAMe was extracted from the dry yeast containing SAMe by a known method using perchloric acid (see, for example, Shiozaki S., et al, Agric. Biol. Chem., 48, 2293-2300 (1984)) and quantitatively determined by liquid chromatography. The liquid chromatography was performed under the following analysis conditions.

Column: Nacalai Tesque, Inc., Cosmosil 4.6 mm in diameter×100 mm

Eluant: 0.2M $KH_2PO_4$ aqueous solution/methanol=95/5 (volume ratio)

Flow rate: 0.7 mL/min

Detector: UV (260 nm)

SAMe retention time: ca. 150 seconds

Examples 2 to 4

The same procedures as in Example 1 were performed except that sulfuric acid was added to the yeast cell concentrate to provide pH 2, 3 or 4, and the relationship between the pH after adding sulfuric acid and the SAMe content after spray drying was investigated. The results are shown in Table 1.

Comparative Example 1

The same procedures as in Example 1 were performed except that sulfuric acid was not added to the yeast cell concentrate to provide 581 g of a powder dry yeast having been spray dried. The resulting powder dry yeast had a SAMe content of 136 mg per gram of dry yeast. The results are shown in Table 1.

Table 1: Relationship between pH after adding mineral acid to yeast cell concentrate and SAMe content of powder dry yeast obtained by spray drying with only treatment of adding mineral acid performed (no treatment of heating)

TABLE 1

| Example | Addition amount of 95% sulfuric acid (g) | pH after adding sulfuric acid | SAMe content in powder dry yeast (mg per gram of dry yeast) |
|---|---|---|---|
| Example 1 | 224 | 1 | 174 |
| Example 2 | 118 | 2 | 171 |
| Example 3 | 57.5 | 3 | 153 |
| Example 4 | 23.6 | 4 | 144 |
| Comparative Example 1 | 0 | 5.2 | 136 |

Example 5

The procedures (a) to (c) were performed in the same manner as in Example 1, and 3.71 kg of a yeast cell concentrate having pH 1 by adding sulfuric acid. The yeast cells having been unheated were poured into a stainless steel tray for freeze drying of a freeze dryer (produced by ULVAC, Inc.) and frozen at −50° C., and then the yeast cells were freeze dried for 36 hours under conditions of a final stage temperature of 25° C. The resulting freeze dried yeast was further pulverized to provide 612 g of powder dry yeast. The resulting powder dry yeast had a SAMe content of 170 mg per gram of dry yeast. The results are shown in Table 2.

Examples 6 to 8

The same procedures as in Example 5 were performed except that sulfuric acid was added to the yeast cell concentrate to provide pH 2, 3 or 4, and the relationship between the pH after adding sulfuric acid and the SAMe content after freeze drying was investigated. The results are shown in Table 2.

Comparative Example 2

The same procedures as in Example 5 were performed except that sulfuric acid was not added to the yeast cell concentrate to provide 609 g of a powder dry yeast having been freeze dried. The resulting powder dry yeast had a SAMe content of 136 mg per gram of dry yeast. The results are shown in Table 2.

Table 2: Relationship between pH after adding mineral acid to yeast cell concentrate and SAMe content of powder dry yeast obtained by freeze drying with only treatment of adding mineral acid performed (no treatment of heating)

TABLE 2

| Example | Addition amount of 95% sulfuric acid (g) | pH after adding sulfuric acid | SAMe content in powder dry yeast (mg per gram of dry yeast) |
|---|---|---|---|
| Example 5 | 224 | 1 | 170 |
| Example 6 | 118 | 2 | 168 |
| Example 7 | 57.5 | 3 | 154 |
| Example 8 | 23.6 | 4 | 143 |
| Comparative Example 2 | 0 | 5.2 | 136 |

Examples 9 to 11

The same procedures as in Example 5 were performed except that sulfuric acid added to the yeast cell concentrate was changed to hydrochloric acid, nitric acid or phosphoric acid (pH of yeast cell concentrate after addition: 1), and the relationship between the addition amount of the mineral acid and the SAMe content after freeze drying was investigated. The results are shown in Table 3.

Table 3: Relationship between pH after adding mineral acid to yeast cell concentrate and SAMe content of powder dry yeast obtained by freeze drying with only treatment of adding mineral acid performed (no treatment of heating)

TABLE 3

| Example | Mineral acid added | Addition amount of mineral acid (g) | pH after adding mineral acid | SAMe content in powder dry yeast (mg per gram of dry yeast) |
|---|---|---|---|---|
| Example 9 | 35% hydrochloric acid | 295 | 1 | 160 |
| Example 10 | 61% nitric acid | 307 | 1 | 155 |
| Example 11 | 85% phosphoric acid | 927 | 1 | 156 |
| Comparative Example 2 | none | 0 | 5.2 | 136 |

Examples 12 to 23 and Comparative Examples 3 to 5

The procedures (a) to (b) were performed in the same manner as in Example 1, and the yeast cell concentrate was subjected to a treatment of heating by using a glass beaker, a magnetic stirrer and a heating water bath to a heating temperature of 40° C., 50° C., 60° C., 70° C. or 90° C. for a time for treatment of heating of 60 seconds, 300 seconds or 600 seconds, and then cooled to 25° C. with a water bath. The concentrate was poured into a stainless steel tray for freeze drying of a freeze dryer (produced by ULVAC, Inc.) and frozen at −50° C., and then the yeast cells were freeze dried for 36 hours under conditions of a final stage temperature of 25° C. The SAMe contents of the resulting powder dry yeasts are shown in Table 4.

Table 4: Relationship between heating temperature and SAMe content of powder dry yeast obtained by freeze drying in yeast cell concentrate subjected to only treatment of heating (no addition of sulfuric acid)

TABLE 4

| | Sulfuric acid not added (pH of yeast cell concentrate before heating: 5.2) | | |
|---|---|---|---|
| Example | Heating temperature (° C.) | Heating time (second) | SAMe content in powder dry yeast (mg per gram of dry yeast) |
| Comparative Example 2 | not heated | — | 136 |
| Example 12 | 40 | 60 | 155 |
| Example 13 | 40 | 300 | 156 |
| Example 14 | 40 | 600 | 155 |
| Example 15 | 50 | 60 | 156 |
| Example 16 | 50 | 300 | 159 |
| Example 17 | 50 | 600 | 158 |
| Example 18 | 60 | 60 | 163 |
| Example 19 | 60 | 300 | 168 |
| Example 20 | 60 | 600 | 164 |
| Example 21 | 70 | 60 | 158 |
| Example 22 | 70 | 300 | 161 |
| Example 23 | 70 | 600 | 155 |
| Comparative Example 3 | 90 | 60 | 127 |
| Comparative Example 4 | 90 | 300 | 109 |
| Comparative Example 5 | 90 | 600 | 73 |

Examples 24 to 32

The procedures (a) to (c) were performed in the same manner as in Example 1, and sulfuric acid was added to a yeast cell concentrate to provide pH 1, 2 or 3. The yeast cell concentrate was subjected to a treatment of heating by using a glass beaker, a magnetic stirrer and a heating water bath to a heating temperature of 60° C. for a time for treatment of heating of 60 seconds, 300 seconds or 600 seconds, and then cooled to 25° C. with a water bath. The yeast cells were poured into a stainless steel tray for freeze drying of a freeze dryer (produced by ULVAC, Inc.) and frozen at −50° C., and then the yeast cells were freeze dried for 36 hours under conditions of a final stage temperature of 25° C. The SAMe contents of the resulting powder dry yeasts are shown in Table 5.

Table 5: Relationship between heating temperature and SAMe content of powder dry yeast obtained by freeze drying in yeast cell concentrate subjected to both treatment of adding mineral acid and treatment of heating (pH of yeast cell concentrate before heating: 1, 2 or 3)

TABLE 5

| Example | pH of yeast cell concentrate before heating | Heating temperature (° C.) | Heating time (second) | SAMe content in powder dry yeast (mg per gram of dry yeast) |
|---|---|---|---|---|
| Example 5 | 1 | not heated | — | 170 |
| Example 24 | 1 | 60 | 60 | 172 |
| Example 25 | 1 | 60 | 300 | 171 |
| Example 26 | 1 | 60 | 600 | 166 |
| Example 6 | 2 | not heated | — | 168 |
| Example 27 | 2 | 60 | 60 | 175 |
| Example 28 | 2 | 60 | 300 | 177 |
| Example 29 | 2 | 60 | 600 | 170 |
| Example 7 | 3 | not heated | — | 154 |
| Example 30 | 3 | 60 | 60 | 176 |
| Example 31 | 3 | 60 | 300 | 179 |
| Example 32 | 3 | 60 | 600 | 173 |

Examples 33 to 41 and Comparative Examples 6 to 8

The procedures (a) to (c) were performed in the same manner as in Example 1, and 3.71 kg of a yeast cell concentrate having pH 3 by adding sulfuric acid. The yeast cell concentrate was subjected to a treatment of heating by using a glass beaker, a magnetic stirrer and a heating water bath to a heating temperature of 40° C., 50° C., 70° C. or 90° C. for a time for treatment of heating of 60 seconds, 300 seconds or 600 seconds, and then cooled to 25° C. with a water bath. The concentrate was poured into a stainless steel tray for freeze drying of a freeze dryer (produced by ULVAC, Inc.) and frozen at −50° C., and then the yeast cells were freeze dried for 36 hours under conditions of a final stage temperature of 25° C. The SAMe contents of the resulting powder dry yeasts are shown in Table 6.

Table 6: Relationship between heating temperature and SAMe content of powder dry yeast obtained by freeze drying in yeast cell concentrate subjected to both treatment of adding mineral acid and treatment of heating (pH of yeast cell concentrate before heating: 3)

TABLE 6

| | Sulfuric acid added (pH of yeast cell concentrate before heating: 3) | | |
|---|---|---|---|
| Example | Heating temperature (° C.) | Heating time (second) | SAMe content in powder dry yeast (mg per gram of dry yeast) |
| Example 7 | not heated | — | 154 |
| Example 33 | 40 | 60 | 154 |
| Example 34 | 40 | 300 | 157 |
| Example 35 | 40 | 600 | 155 |
| Example 36 | 50 | 60 | 154 |
| Example 37 | 50 | 300 | 164 |
| Example 38 | 50 | 600 | 162 |
| Example 30 | 60 | 60 | 176 |
| Example 31 | 60 | 300 | 179 |
| Example 32 | 60 | 600 | 173 |
| Example 39 | 70 | 60 | 172 |
| Example 40 | 70 | 300 | 163 |
| Example 41 | 70 | 600 | 155 |
| Comparative Example 6 | 90 | 60 | 140 |
| Comparative Example 7 | 90 | 300 | 118 |
| Comparative Example 8 | 90 | 600 | 81 |

[Industrial Applicability]

According to the present invention, a dry yeast containing SAMe in a high concentration can be produced conveniently with a good yield at low cost. A composition for oral ingestion formed by molding the dry yeast containing SAMe can be used widely as a therapeutic medication for depression, liver disorder, arthritis and the like, or health foods.

The invention claimed is:

1. A method for producing a dry yeast containing S-adenosyl-L-methionine using a yeast having production capability of S-adenosyl-L-methionine, comprising:

(i) separating a yeast cell concentrate from a cell culture liquid of the yeast;

(ii) adding a mineral acid to the yeast cell concentrate to adjust the pH to a value within a range of 1 to 4;

(iii) subsequent to adding the mineral acid, heating the concentrate at a temperature within a range of 40° to 70° C.; and (iv) after the heating, drying the concentrate.

2. The method for producing a dry yeast containing S-adenosyl-L-methionine according to claim 1, wherein a yeast belonging to *Saccharomyces* is used as the yeast having production capability of S-adenosyl-L-methionine.

3. The method for producing a dry yeast containing S-adenosyl-L-methionine according to claim 2, wherein the yeast belonging to *Saccharomyces* is *Saccharomyces cerevisiae*.

4. The method for producing a dry yeast containing S-adenosyl-L-methionine according to claim 1, wherein the mineral acid used in the treatment of adding a mineral acid is sulfuric acid.

5. The method for producing a dry yeast containing S-adenosyl-L-methionine according to claim 1, wherein the concentrate is dried by a freeze drying method or a spray drying method.

6. The method for producing a dry yeast containing S-adenosyl-L-methionine according to claim 1, wherein the mineral acid is added to the yeast cell concentrate to adjust the pH to a value within a range of 1 to 3.

7. The method for producing a dry yeast containing S-adenosyl-L-methionine according to claim 1, wherein the heating is performed for a time within a range of 30 to 600 seconds.

8. The method for producing a dry yeast containing S-adenosyl-L-methionine according to claim 1, wherein the heating is performed for a time within a range of 30 to 60 seconds.

9. The method for producing a dry yeast containing S-adenosyl-L-methionine according to claim 1, wherein the heating is performed at a temperature of 50° to 70° C.

* * * * *